(12) United States Patent
DeFreitas et al.

(10) Patent No.: US 10,729,403 B2
(45) Date of Patent: Aug. 4, 2020

(54) SYSTEM AND METHOD FOR FUSING THREE DIMENSIONAL IMAGE DATA FROM A PLURALITY OF DIFFERENT IMAGING SYSTEMS FOR USE IN DIAGNOSTIC IMAGING

(71) Applicant: HOLOGIC INC., Marlborough, MA (US)

(72) Inventors: Kenneth F. DeFreitas, Patterson, NY (US); Ian Shaw, Yorktown Heights, NY (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 15/904,689

(22) Filed: Feb. 26, 2018

(65) Prior Publication Data

US 2018/0249985 A1    Sep. 6, 2018

Related U.S. Application Data

(63) Continuation of application No. 13/325,495, filed on Dec. 14, 2011, now Pat. No. 9,901,320.

(Continued)

(51) Int. Cl.
*A61B 8/08* (2006.01)
*A61B 8/00* (2006.01)
(Continued)

(52) U.S. Cl.
CPC ............ *A61B 8/0825* (2013.01); *A61B 6/025* (2013.01); *A61B 6/0414* (2013.01); *A61B 6/12* (2013.01);
(Continued)

(58) Field of Classification Search
None
See application file for complete search history.

(56) References Cited

U.S. PATENT DOCUMENTS 3,908,293 A * 9/1975 Newman ................. B41F 15/36
                                                        101/127.1
3,971,950 A * 7/1976 Evans .................... A61B 6/502
                                                        378/37
(Continued)

FOREIGN PATENT DOCUMENTS

DE        103 05 640        8/2003
JP        2003-527880       9/2003
(Continued)

OTHER PUBLICATIONS

Blane, C. et al., "New Compression Paddle for Wire Localization in Mammography", Academic Radiology, 17(2): 142-145 (2010).
(Continued)

*Primary Examiner* — Katherine L Fernandez

(57) ABSTRACT

A multi-modality cancer screening and diagnosis system is provided that allows cancer screening and diagnosis of a patient using at least two different and sequential three-dimensional imaging techniques without patient repositioning. The system includes a first three-dimensional image acquisition device, a second three-dimensional image acquisition device having a probe with a transmitter mounted thereon, and a positioning paddle for positioning and immobilizing an object to be imaged during the cancer screening and diagnosis procedure. The positioning paddle is designed to facilitate visualization of the breast in both three-dimensional modalities without movement of the patient, and preferably is designed to position the patient with comfort during a diagnosis procedure which uses both imaging modalities.

16 Claims, 8 Drawing Sheets

Related U.S. Application Data

(60) Provisional application No. 61/422,991, filed on Dec. 14, 2010.

(51) Int. Cl.
*A61B 6/02* (2006.01)
*A61B 6/04* (2006.01)
*A61B 6/12* (2006.01)
*A61B 6/00* (2006.01)

(52) U.S. Cl.
CPC ............ *A61B 6/4417* (2013.01); *A61B 6/463* (2013.01); *A61B 6/466* (2013.01); *A61B 6/469* (2013.01); *A61B 6/502* (2013.01); *A61B 6/5247* (2013.01); *A61B 6/563* (2013.01); *A61B 6/566* (2013.01); *A61B 8/0841* (2013.01); *A61B 8/0866* (2013.01); *A61B 8/4245* (2013.01); *A61B 8/4263* (2013.01); *A61B 8/4416* (2013.01); *A61B 8/4438* (2013.01); *A61B 8/466* (2013.01); *A61B 8/469* (2013.01); *A61B 8/483* (2013.01); *A61B 8/486* (2013.01); *A61B 8/5261* (2013.01)

(56) References Cited

U.S. PATENT DOCUMENTS

| | | |
|---|---|---|
| 4,907,156 A | 3/1990 | Doi |
| 5,133,020 A | 7/1992 | Giger |
| 5,220,867 A * | 6/1993 | Carpenter ............... B41F 15/36 101/127.1 |
| 5,289,374 A | 2/1994 | Doi |
| 5,343,390 A | 8/1994 | Doi |
| 5,452,367 A | 9/1995 | Bick |
| 5,474,072 A | 12/1995 | Schmulewitz |
| 5,479,603 A | 12/1995 | Stone |
| 5,491,627 A | 2/1996 | Zhang |
| 5,495,576 A | 2/1996 | Ritchey |
| 5,537,485 A | 7/1996 | Nishikawa |
| 5,657,362 A | 8/1997 | Giger |
| 5,729,471 A | 3/1998 | Jain |
| 5,851,180 A * | 12/1998 | Crosby ................ A61B 6/0414 600/407 |
| 5,999,662 A | 12/1999 | Burt |
| 6,044,181 A | 3/2000 | Szeliski et al. |
| 6,075,905 A | 6/2000 | Herman et al. |
| 6,104,840 A | 8/2000 | Ejiri et al. |
| 6,198,838 B1 | 3/2001 | Roehrig |
| 6,249,616 B1 | 6/2001 | Hashimoto |
| 6,263,092 B1 | 7/2001 | Roehrig |
| 6,349,153 B1 | 2/2002 | Teo |
| 6,359,617 B1 | 3/2002 | Xiong |
| 6,725,095 B2 | 4/2004 | Fenn |
| 7,054,473 B1 | 5/2006 | Roehrig |
| 7,123,684 B2 | 10/2006 | Jing et al. |
| 7,134,080 B2 | 11/2006 | Kjeldsen |
| 7,174,039 B2 | 2/2007 | Koo |
| 7,245,694 B2 | 7/2007 | Jing et al. |
| 7,489,761 B2 | 2/2009 | Clause |
| 7,505,555 B2 | 3/2009 | Hermann |
| 7,702,142 B2 | 4/2010 | Ren |
| 7,731,662 B2 | 6/2010 | Anderson et al. |
| 8,160,677 B2 | 4/2012 | Gielen et al. |
| 8,192,361 B2 | 6/2012 | Sendai |
| 8,465,413 B2 | 6/2013 | Deitch |
| 8,942,342 B2 | 1/2015 | Abenaim |
| 9,160,793 B2 | 10/2015 | Base et al. |
| 9,901,320 B2 | 2/2018 | DeFreitas et al. |
| 2001/0044578 A1 | 11/2001 | Ben-Haim et al. |
| 2003/0007598 A1 | 1/2003 | Wang et al. |
| 2003/0055471 A1 | 3/2003 | Fenn et al. |
| 2003/0194050 A1 | 10/2003 | Eberhard et al. |
| 2004/0077944 A1 | 4/2004 | Steinberg |
| 2005/0089205 A1 * | 4/2005 | Kapur ................ A61B 6/4233 382/128 |
| 2005/0108643 A1 | 5/2005 | Schybergson |
| 2006/0074287 A1 | 4/2006 | Neumann |
| 2006/0126794 A1 | 6/2006 | Hermann et al. |
| 2007/0167709 A1 | 7/2007 | Slayton |
| 2007/0232882 A1 | 10/2007 | Glossop |
| 2007/0280412 A1 * | 12/2007 | Defreitas ............. A61B 6/0414 378/37 |
| 2008/0181361 A1 * | 7/2008 | Eldered .................... A61B 6/04 378/37 |
| 2008/0242968 A1 | 10/2008 | Claus et al. |
| 2009/0118614 A1 | 5/2009 | Sendai |
| 2009/0124906 A1 | 5/2009 | Caluser |
| 2009/0175408 A1 * | 7/2009 | Goodsitt .............. A61B 6/0414 378/37 |
| 2010/0016707 A1 | 1/2010 | Amara et al. |
| 2010/0166147 A1 | 7/2010 | Abenaim |
| 2011/0313288 A1 | 12/2011 | Chi Sing |
| 2012/0035462 A1 | 2/2012 | Maurer et al. |
| 2012/0256920 A1 | 10/2012 | Marshall et al. |

FOREIGN PATENT DOCUMENTS

| | | |
|---|---|---|
| JP | 2005125080 | 5/2005 |
| JP | 2007-515242 | 6/2007 |
| JP | 2008518722 | 6/2008 |
| JP | 2009502347 | 1/2009 |
| JP | 2009-518722 | 5/2009 |

OTHER PUBLICATIONS

Bram Van Ginneken, Computer-aided Diagnosis in Chest Radiography Thesis, Image Sciences Institute, University Medical Center Utrecht, Utrecht, Netherlands.

Carson, P. et al., "Local compression in automated breast ultrasound in the mammographic geometry", Ultrasonics Symposium, 1787-1790 (2010).

European Extended Search Report for corresponding European Patent Application No. 11848276.9 dated Aug. 9, 2016, 13 pgs.

Giger et al., An Intelligent Workstation for Computer Aided Diagnosis, RadioGraphics May 1993, vol. 13, pp. 647-656.

Giger et al., Development of a Smart Workstation for Use in Mammography, SPIE, vol. 1445, 1991, pp. 101-103.

Gutierrez et al., "Multimodality image guidance system integrating X-ray fluoroscopy and ultrasound image streams with electromagnetic tracking", Medical Imaging 2007: Visualization and Image-Guided Procedures, Proc. of SPIE vol. 6509, 2007, pp. 1-10.

PCT International Search Report and Written Opinion for PCT/US2011/064847, dated Jun. 7, 2012.

PCT International Preliminary Report on Patentability for PCT/US2011/064847, dated Jun. 18, 2013, 8 pages.

* cited by examiner

SYSTEM AND METHOD FOR FUSING THREE DIMENSIONAL IMAGE DATA FROM A PLURALITY OF DIFFERENT IMAGING SYSTEMS FOR USE IN DIAGNOSTIC IMAGING

RELATED APPLICATIONS

This application is a continuation of U.S. application Ser. No. 13/325,495, filed Dec. 14, 2011, now U.S. Pat. No. 9,901,320 entitled "System and Method for Fusing Three Dimensional Image Data from a Plurality of Different Imaging Systems for Use in Diagnostic Imaging," which is related to, and claims priority under 35 U.S.C. 1.119(e) to U.S. Provisional Application Ser. No. 61/422,991, filed Dec. 14, 2010, entitled "A Tomo/Ultrasound Fusion Device for Diagnostic Imaging," the disclosures of which are hereby incorporated by reference herein in their entireties.

This application is related to U.S. patent application Ser. No. 12/954,633, filed on Nov. 25, 2010 by the same assignee as the present application, and entitled "SYSTEMS AND METHOD FOR TRACKING POSITIONS BETWEEN IMAGING MODALITIES AND TRANSFORMING A DISPLAYED THREE-DIMENSIONAL IMAGE CORRESPONDING TO A POSITION AND ORIENTATION OF A PROBE," which claims priority to U.S. Provisional Application 61/264,743, filed Nov. 27, 2009 and U.S. Provisional Application 61/394,734, filed Oct. 19, 2010, all of which are incorporated herein by reference.

BACKGROUND

Medical imaging devices provide non-invasive methods to visualize the internal structure of a patient. Such non-invasive visualization methods can be helpful in treating patients for various ailments. For example, the early detection of cancer in a patient can be important in treating that patient. For most cancers, when detected at an early stage, the survival probability of the patient can increase.

In the U.S. breast cancer mortality is second only to that of lung cancer. Because of its role in early tumor detection, mammography has become the most commonly used tool for breast cancer screening, diagnosis and evaluation in the United States. A mammogram is an x-ray image of inner breast tissue that is used to visualize normal and abnormal structures within the breasts. Mammograms provide early cancer detection because they can often show a breast lumps and/or calcifications before they are manually palpable. One drawback of mammography is that it provides only a two-dimensional representation of a compressed breast, and as a result masses which are hidden by intervening structures may not always be readily discernible on a mammogram.

Tomosynthesis systems, which are x-ray systems for obtaining a three dimensional image volume of a breast, have recently been developed for use in breast cancer screening. One such tomosynthesis system, the Selenia® Dimensions® breast tomosynthesis system, is provided by Hologic, Inc., of Bedford Mass., the assignee of the present invention. In contrast to typical mammography systems, the tomosynthesis system acquires a series of x-ray projection images, each projection image obtained at a different angular displacement as the x-ray source traverses along a path over the breast. Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. Nos. 7,245,694 and 7,123,684, commonly owned by the Assignee of this application and incorporated by reference herein.

While mammography (and now tomosynthesis systems) have become the 'gold standard' for breast cancer screening, if the screening identifies a lump or a mass the standard protocol recommends review of the patient using a different imaging modality such as ultrasound imaging, to further characterize the mass or region of interest during breast cancer diagnosis.

Ultrasound imaging, another non-invasive medical imaging technique, uses sound waves, typically produced by piezoelectric transducers to image a tissue in a patient. The ultrasound probe focuses the sound waves, typically producing an arc-shaped sound wave which travels into the body and is partially reflected from the layers between different tissues in the patient. The reflected sound wave is detected by the transducer and converted into electrical signals that can be processed by the ultrasound scanner to form an ultrasound image of the tissue.

The typical procedure followed to obtain ultrasound images of a patient's breast involves positioning a patient in a supine position upon a table, applying a gel or other acoustic couplant to the patient's breast, and passing an ultrasound transducer across the patient's breast. As the transducer traverses the breast, ultrasound images can typically be viewed in real-time on a display of an ultrasound system. The ultrasound transducer may be either a hand-held transducer which is manually manipulated by the imaging technician, or may be an automated scanning device, such as that described in U.S. Pat. No. 7,731,662. One drawback of such methods lies in the fact that the breast is a very malleable structure; the geometry and structures of the breast move and change whenever the patient changes position. Thus, a mass which is readily identified when a patient is positioned for imaging using a first modality may be difficult to detect when the patient is repositioned for examination using a second modality.

SUMMARY OF THE INVENTION

According to one aspect of the invention, a multi-modality cancer screening and diagnosis system is provided that allows cancer screening and diagnosis of a patient using at least two different and sequential three-dimensional imaging techniques without patient repositioning. The system comprises a first three-dimensional image acquisition device, a second three-dimensional image acquisition device having a probe with a transmitter mounted thereon, and a positioning paddle for positioning and immobilizing an object to be imaged during the cancer screening and diagnosis procedure. Although the present invention is not to be limited, in one embodiment, the object to be imaged is a patient's breast, and the position of the patient for screening and diagnosis is an upright position. The positioning paddle is designed to facilitate visualization of the breast in both three-dimensional modalities without movement of the patient, and preferably is designed to position the patient with comfort during a diagnosis procedure which uses both imaging modalities.

According to another aspect of the invention, a method of examining an object for diagnosis purposes includes the steps of positioning the object prior to a diagnosis process using a positioning mechanism, acquiring a three dimensional image of the object using a first imaging modality, displaying the three dimensional image of the object, and, during a diagnosis process, acquiring real-time three-dimensional images of the object using a transmitting probe and comparing the three dimensional images acquired using the first imaging modality to the three dimensional images of the object acquired using the transmitting probe. Following the diagnosis process the positioned object is released. In one embodiment the positioned object is a patient's breast, and a mechanism that is used to position the patients breast is a positioning paddle that enables image acquisition using multiple three-dimensional imaging modalities while the patient remains in one position, and preferably while maintaining patient comfort.

Such an arrangements overcome the problems of breast cancer screening and diagnosis in the prior art, which typically requires a patient to move between the preferred, upright screening position to a supine position for further diagnosis, often making it difficult for the radiologist to ensure that they have located the region of interest identified during the screening process.

These and other aspects of the present invention will be described in more detail with regard to the Figures identified below.

DETAILED DESCRIPTION

A multi-modality cancer screening and diagnosis system will now be described which enables screening and diagnosis of a patient to be performed using multiple three-dimensional image acquisition systems while maintaining constant patient positioning. A positioning paddle, suitable for use in two different and distinct imaging modalities, helps to achieve this result. The system will be described with regard to the screening and diagnosis of a patient's breast, using an upright three-dimensional x-ray system (an in particular, a tomosynthesis imaging system) as a first imaging modality, and a three-dimensional ultrasound imaging system as a second modality, although it should be understood that the present invention is not limited to these particular imaging modalities. For example, the present invention may be used with three-dimensional images acquired via stereotactic x-ray acquisition, SPECT, PET, gamma, or other Computed Tomography image acquisition systems and the like.

It is understood that fusing images obtained from different imaging modalities, and even with regard to breast cancer screening, is not new to the art. For example, in U.S. Pat. No. 5,474,072, entitled "Methods and Apparatus for Performing Sonomammography" Schmulewitz describes a method and apparatus for combining a mammography machine with an ultrasound transducer, to generate ultrasound images that are in registration with a mammogram. Drawbacks of the '072 patent include the fact that only two-dimensional data is obtained via the mammogram, and that the path of the ultrasound probe is pre-determined, removing the opportunity for real-time manual manipulation.

U.S. Patent Application No. US20030194050, entitled "Multi modality X-ray and nuclear medicine mammography imaging system and method" describes a multi modality imaging system that includes an X-ray imaging subsystem and a nuclear medicine imaging subsystem, where the X-ray imaging subsystem may be a tomosynthesis subsystem. The system may be used for mammography imaging, such that the X-ray imaging subsystem and the nuclear medicine imaging subsystem are adapted to image a breast compressed by a breast compression paddle. Similar to the '072 patent, the system described in the '050 application does not allow for real-time manual manipulation of the second imaging modality. In addition, both systems position the patient in compression, which may become uncomfortable for the patient during prolonged diagnosis. Further, the arrangement of the compression plates and imaging devices in both systems preclude the ability to perform any interventional procedures, such as breast biopsy, when the patient is positioned within these configurations.

Figure 1:
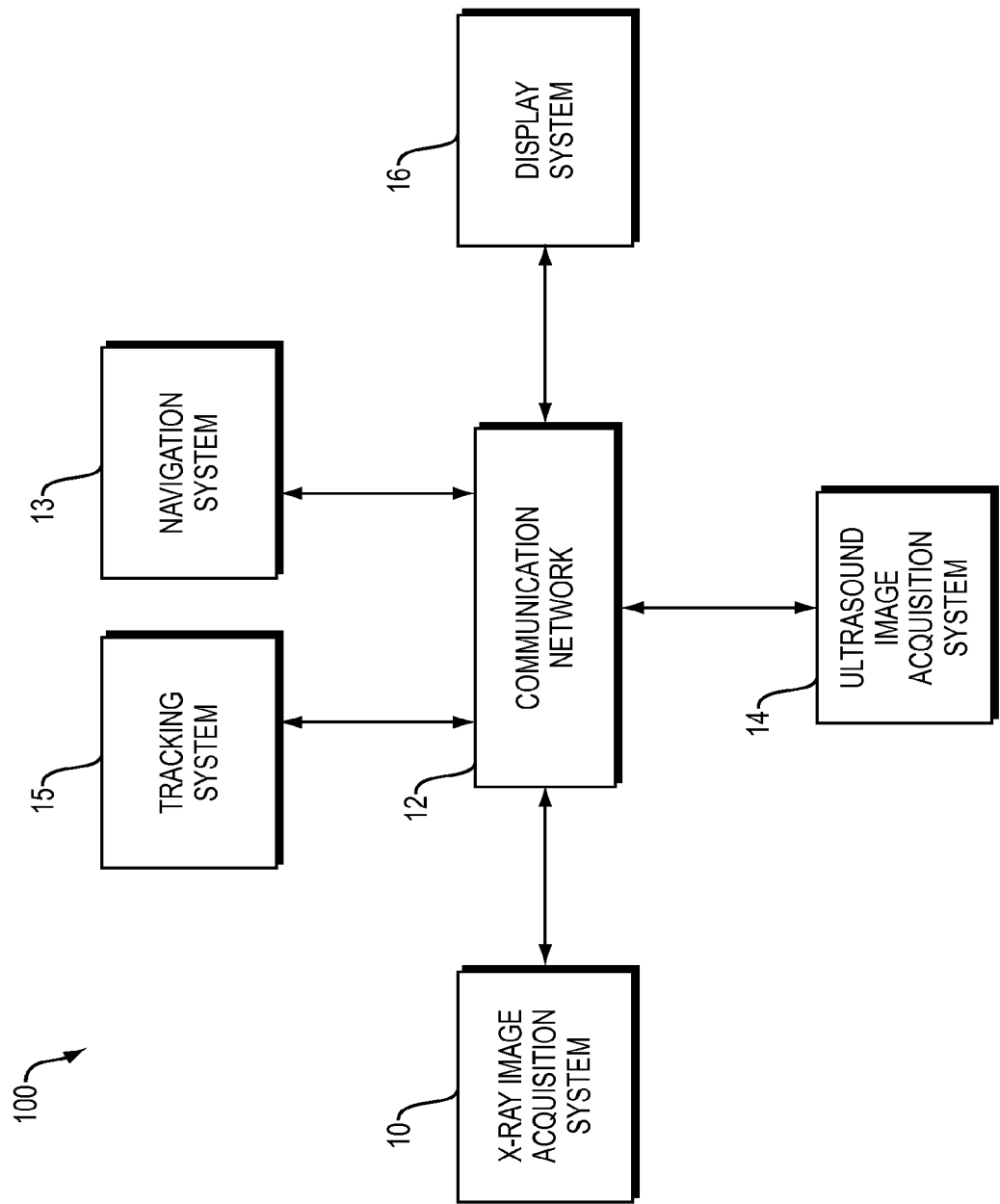
FIG. 1 is a block diagram of one embodiment of a system which permits fusion of x-ray images and ultrasound images for breast cancer diagnosis.

In contrast, as will become apparent from review of the detailed description, the present invention facilitates screening and diagnosis of the patient in comfort, using information from at least two three-dimensional image acquisition devices, at least one of which may be manipulated in real time. For example, referring now to FIG. 1, an embodiment of system 100 is shown. System 100 includes an X-RAY image acquisition device 10, a tracking system 15, an ultrasound imaging system 14, a navigation system 13 and a display system 16, all representatively connected via communication network 12. It should be noted that, although the 'systems' are shown in FIG. 1 as functional blocks, different systems may be integrated into a common device, and the communication link may be coupled between fewer than all of the systems; for example, the tracking system, navigation system and display system may be included in an acquisition work station or a technologist work station which may control the acquisition of the x-ray images in a radiology suite. Alternatively, the navigation and tracking systems may be integrated into the ultrasound system, or provided as standalone modules with separate communication links to the display, x-ray acquisition system and ultrasound system. Similarly, skilled persons will additionally appreciate that communication network 12 can be a local area network, wide area network, wireless network, internet, intranet, or other similar communication network.

In one embodiment, X-Ray image acquisition system 10 is a tomosynthesis acquisition system which captures a set of projection images of a patient's breast as an x-ray tube scans across a path over the breast. The set of projection images is subsequently reconstructed to a three-dimensional volume which may be viewed as slices or slabs along any plane. The three-dimensional volume may be stored locally on X-RAY imaging system 10 or in some embodiments in a Picture Archiving Communications System (PACS). Typically, the image format of the X-RAY image is a DICOM format, however, skilled persons will understand that other image formats can be used.

X-RAY imaging system 10 transmits the three-dimensional X-RAY image volume to navigation system 13 via communication network 12, where such X-RAY image can be stored and viewed. Skilled persons will understand that the X-RAY image of a patient can, in alternative embodiments, be stored locally on X-RAY imaging system 10 and accessed remotely by navigation system 13 via communications network 12, and in other embodiments can be stored on a server in communication with navigation system 13 via communications network 12. Navigation system 13 displays the X-RAY image obtained by X-RAY imaging system and once reconstructed for display on navigation system 13 the X-RAY image can be reformatted and repositioned to view the image at any plane and any slice position or orientation. In some embodiments navigation system 13 displays multiple frames or windows on the same screen showing alternative positions or orientations of the X-RAY-image slice.

Skilled persons will understand that the X-RAY image volume obtained by X-RAY imaging system 10 can be transmitted to navigation system 13 at any point in time and is not necessarily transmitted immediately after obtaining the X-RAY image volume, but instead can be transmitted on the request of navigation system 13. In alternative embodiments, the X-RAY image volume is transmitted to navigation system 13 by a transportable media device, such as a flash drive, CD-ROM, diskette, or other such transportable media device.

Ultrasound imaging system 14 obtains an ultrasound image of a tissue of a patient, typically using an ultrasound probe, which is used to image a portion of a tissue of a patient within the field of view of the ultrasound probe. Ultrasound imaging system 14 obtains and displays an ultrasound image of a patient's anatomy within the field of view of the ultrasound probe and typically displays the image in real-time as the patient is being imaged. In some embodiments, the ultrasound image can additionally be stored on a storage medium, such as a harddrive, CD-ROM, flash drive or diskette, for reconstruction or playback at a later time.

In some embodiments, navigation system 13 can access the ultrasound image, and in such embodiments ultrasound imaging system 14 is further connected to communication network 12 and a copy of the ultrasound image obtained by ultrasound imaging system 14 can be transmitted to navigation system 13 via communication network 12. In other embodiments, navigation system 13 can remotely access and copy the ultrasound image via communication network 12, and in alternative embodiments, a copy of the ultrasound image can be stored on a server in communication with navigation system 13 via communications network 12 and accessed remotely by navigation system 13.

Tracking system 15 is in communication with navigation system 13 via communications network 12 and tracks the physical position in which ultrasound imaging system 14 is imaging the tissue of the patient. In some embodiments, tracking system 15 can be connected directly to navigation system 13 via a direct communication link or wireless communication link. Tracking system 15 tracks the position of transmitters connected to ultrasound imaging system 14 and provides navigation system 13 with data representing their coordinates in a tracker coordinate space. In some embodiments, tracking system may be an optical tracking system comprising an optical camera and optical transmitters, however skilled persons will understand that any device or system capable of tracking the position of an object in space can be used. For example, skilled persons will understand that in some embodiments an RF tracking system can be used, comprising an RF receiver and RF transmitters.

Ultrasound imaging system 14 is configured for use with navigation system 13 by a calibration process using tracking system 15. Transmitters that are removably connected to the ultrasound probe of ultrasound imaging system 14 can transmit their position to tracking system 13 in the tracker coordinate space, which in turn provides this information to navigation system 13. For example, transmitters may be positioned on the probe of ultrasound imaging system 14 so that tracking system 15 can monitor the position and orientation of the ultrasound probe and provide this information to navigation system 13 in the tracker coordinate space. Navigation system 13 can use this tracked position to determine the position and orientation of the transducer, an ultrasound probe, relative to the tracked position of the transmitters.

In some embodiments, configuration occurs using a configuration tool, where its position and orientation can be additionally tracked by tracking system 15. During configuration the configuration tool contacts the transducer face of the ultrasound probe of ultrasound imaging system 14 and tracking system 15 transmits information representing the position and orientation of the configuration tool in the tracker coordinate space to navigation system 13. Navigation system 13 can determine a configuration matrix that can be used to determine the position and orientation of the field of view of the ultrasound probe in the tracker co-ordinate space, based on the tracked position of the transmitters connected to the ultrasound probe. In alternative embodiments, a database having configuration data of a plurality of brands or models of various ultrasound probes can be used to pre-load a field of view configuration into navigation system 13 during configuration.

Once ultrasound imaging system 14 is configured with navigation system 13, the tissue of a patient can be imaged with ultrasound imaging system 14. During ultrasound imaging, tracking system 15 monitors the position and orientation of the ultrasound probe of ultrasound imaging system 14 and provides this information in the tracker co-ordinate space to navigation system 13. Since ultrasound imaging system 14 has been configured for use with navigation system 13, navigation system 13 is able to determine position and orientation of the field of view of the ultrasound probe of ultrasound imaging system 14.

Navigation system 13 can be configured to co-register an ultrasound image with an X-RAY image. In some embodiments, navigation system 13 can be configured to transform the position and orientation of the field of view of the ultrasound probe from the tracker co-ordinate space to a position and orientation in the X-RAY image, for example, to DICOM co-ordinates. This can be accomplished by tracking the position and orientation of the ultrasound probe and transmitting this positional information in the tracker co-ordinate space to navigation system 13 and relating this positional information to the X-RAY co-ordinate system. For example, in some embodiments, a user can select an anatomical plane within the X-RAY image, and the user can then manipulate the position and orientation of a tracked ultrasound probe to align the field of view of the ultrasound probe with the selected anatomical plane. Once alignment is achieved, the associated tracker co-ordinate space co-ordinates of the ultrasound image can be captured. Registration of the anatomic axes (superior-inferior (SI), left-right (LR) and anterior-posterior (AP)) between the X-RAY image and the tracker co-ordinate space can be determined from the relative rotational differences between the tracked ultrasound field of view orientation and the selected anatomical plane using techniques known to those of skill in the art.

This configuration further includes the selection of landmark within the X-RAY image, for example, using an interface permitting a user to select an anatomical target. In some embodiments, the landmark can be an internal tissue landmark, such as veins or arteries, and in other embodiments, the landmark can be an external landmark, such as a fiducial skin marker or external landmark, such as a nipple. The same landmark selected in the X-RAY image can be located with the ultrasound probe, and upon location, a mechanism can be provided for capturing coordinates of the representation of the target in the tracker co-ordinate space. The relative differences between the coordinates of the target in the X-RAY image and the co-ordinates of the target in the tracker co-ordinate space are used to determine the translational parameters required to align the two co-ordinate spaces. The plane orientation information acquired previously can be combined with the translation parameters to provide a complete 4×4 transformation matrix capable of co-registering the two co-ordinate spaces.

Navigation system 13 can then use the transformation matrix to reformat the X-RAY image being displayed so that the slice of tissue being displayed is in the same plane and in the same orientation as the field of view of the ultrasound probe of ultrasound imaging system 14. Matched ultrasound and X-RAY images may then be displayed side by side, or directly overlaid in a single image viewing frame. In some embodiments, navigation system 13 can display additional X-RAY images in separate frames or positions on a display screen. For example, the X-RAY image can be displayed with a graphical representation of the field of view of ultrasound imaging system 14 wherein the graphical representation of the field of view is shown slicing through a 3D representation of the X-RAY image. In other embodiments annotations can be additionally displayed, these annotations representing, for example, the position of instruments imaged by ultrasound imaging system 14, such as biopsy needles, guidance wires, imaging probes or other similar devices.

In other embodiments, the ultrasound image being displayed by ultrasound imaging system 14 can be superimposed on the slice of the X-RAY image being displayed by navigation system 13 so that a user can view both the X-RAY and ultrasound images simultaneously, overlaid on the same display. In some embodiments, navigation system 13 can enhance certain aspects of the super imposed ultrasound or X-RAY images to increase the quality of the resulting combined image.

An exemplary Method and system which may be used to navigate between a three dimensional image data set and an ultrasound feed, and to align coordinate systems to enable display of common reference points is described in further detail below, as well as in co-pending patent application serial number U.S. patent application Ser. No. 12/954,633, (hereinafter the '633 application) filed on Nov. 25, 2010 by the same assignee as the present application, and entitled "SYSTEMS AND METHOD FOR TRACKING POSITIONS BETWEEN IMAGING MODALITIES AND TRANSFORMING A DISPLAYED THREE-DIMENSIONAL IMAGE CORRESPONDING TO A POSITION AND ORIENTATION OF A PROBE", which claims priority to U.S. Provisional Application 61/264,743, filed Nov. 27, 2009 and U.S. Provisional Application 61/394,734, filed Oct. 19, 2010, all of which are incorporated herein by reference.

Figure 2:
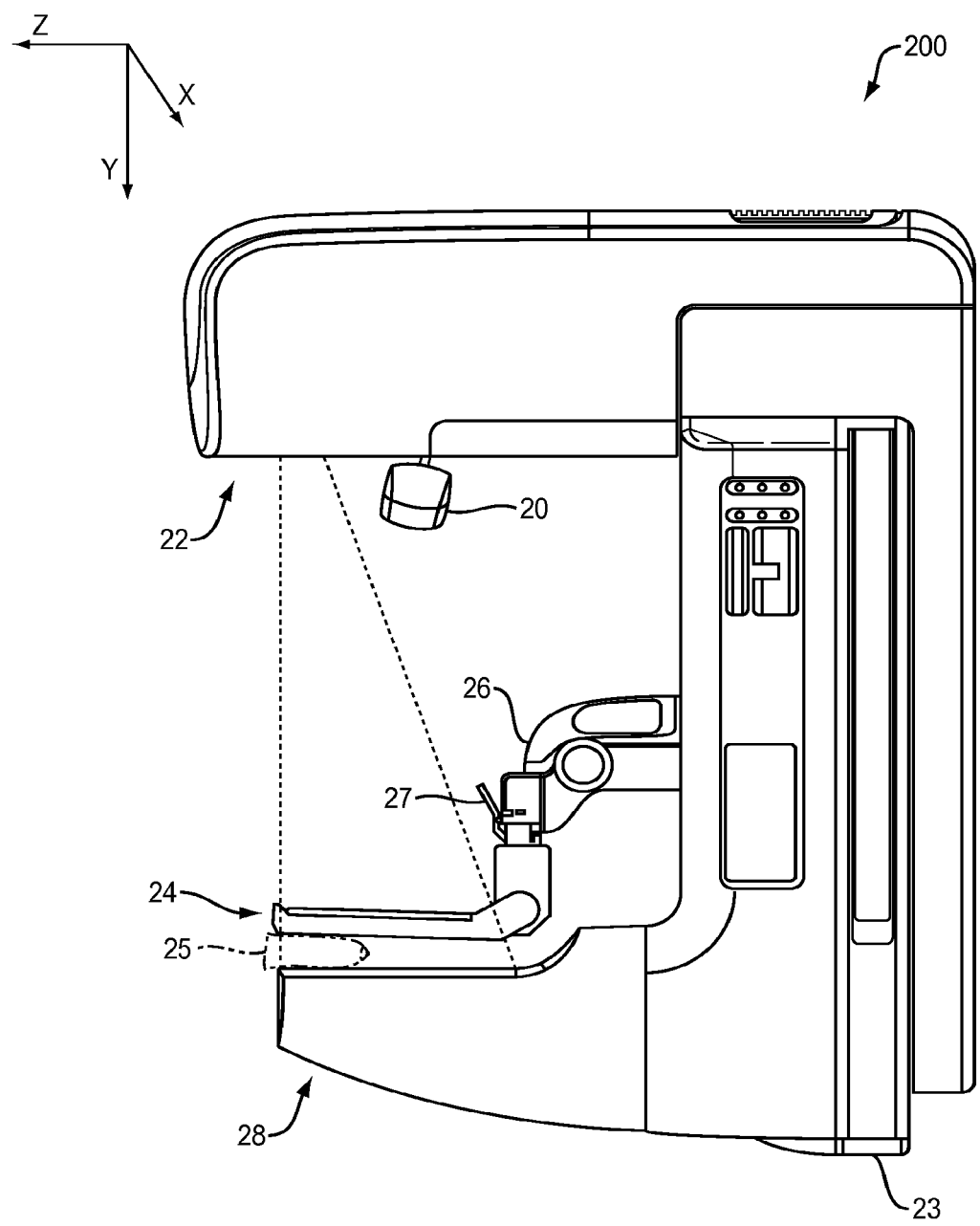
FIG. 2 is a side view an x-ray imaging gantry including a positioning paddle according to the present invention, and having navigation hardware removably mounted thereon.

FIG. 2 illustrates an embodiment of an x-ray gantry which has been modified to incorporate components of the tracking system 15 and a positioning paddle 24 of the present invention. The gantry 200 includes an x-ray tube housing portion 22, an upright portion 23 and a detector housing portion 28. The upright portion is generally slideably mounted on a fixed base device (not shown), which allows the gantry to be positioned below a patients breast to facilitate examination. The x-ray tube housing portion is rotatably coupled to the upright portion 23, allowing x-ray images to be captured both in multiple orientations and using multiple modalities (i.e., CC, MLO, mammography, tomosynthesis, sterotactic). Mounted within the x-ray tube housing is an x-ray source (not shown). An optical camera 20, which is part of the tracking system 15, may be removably or fixedly mounted to the x-ray tube housing 22. One advantage of positioning the optical camera 20 in a fixed manner relative to the positioned breast is that it facilitates co-registration of the three-dimensional volume and the ultrasound transducer. An immobilization arm 26, is slideably mounted for movement along the Y axis to an upright portion 23 of the gantry 200. The immobilization arm 26 may include a latch 27 to permit coupling of interchangeable breast positioning paddles. In FIG. 2, a breast phantom 25 is shown positioned on the detector housing 28 using a breast positioning paddle 24 of the present invention. Prior to screening or diagnosis, a patient is positioned, facing the gantry 200, and the patient's breast may be placed on the surface of the detector housing. The compression arm 26 moves downward, positioning the paddle 24 over the patient's breast. The pressure used to position the patient's breast is sufficient only to immobilize the breast to discourage movement of tissue during the screening and diagnostic procedure.

As discussed above, during a tomosynthesis image acquisition procedure, the x-ray tube head is rotated along a path generally in the x plane, and x-ray projection images are captured at various points along the scan path of the x-ray tube. For example, referring to FIG. 2, the x-ray tube head generally traverses in a direction normal to the reader, which has been indicated as the x-plane in FIG. 2.

Figure 3:
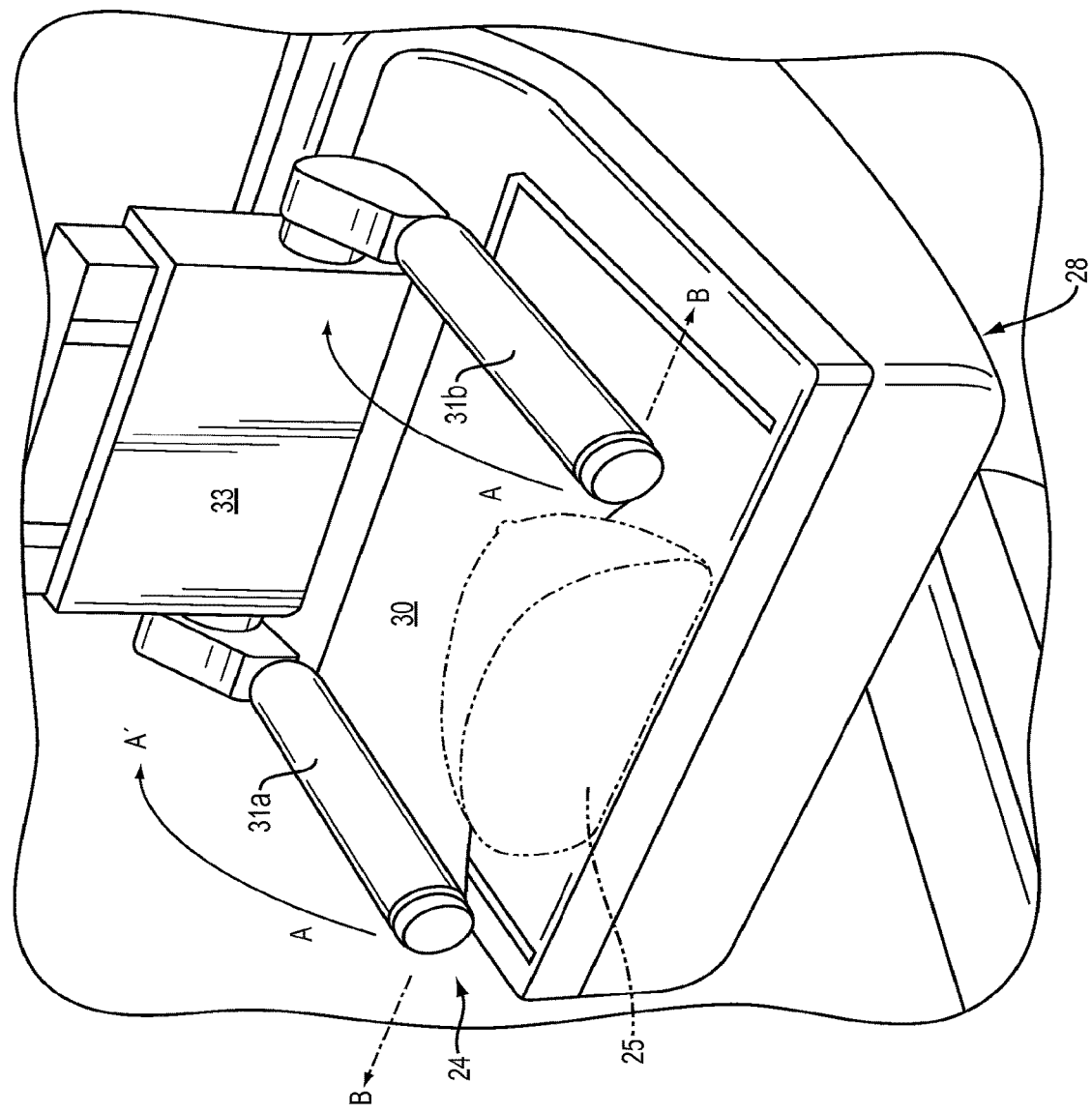
FIG. 3 illustrates in more detail an embodiment of a positioning paddle which may be provided on the gantry of FIG. 2.

FIG. 3 illustrates the positioning paddle 24 in greater detail. As will be described, the positioning paddle is suitable for use in at least two separate and distinct imaging modalities, i.e., image modalities that image using different sources, such as x-ray imaging and ultrasound imaging. According to one aspect of the invention, a positioning paddle suitable for three-dimensional image generation across multiple modalities includes a material 30, positioned between a pair of opposing arms 31a and 31b, wherein each of the arms are attached to a base 33. The material is sufficiently sheer to be transparent to x-rays, and therefore does not interfere with the x-ray image. In one embodiment, the material is formed from a porous fabric, for example a polyester or nylon blend fabric, such as tulle or the like. The material may be inelastic, or may be formed of a material with a limited amount of elasticity. Characteristics of the material is that it should be generally radiolucent, have sufficient porosity to enable acoustic couplant applied to a first surface to reach a second surface and be of sufficient tensile strength and elasticity to immobilize a breast during screening and diagnosis. Additional desirable characteristics are that the material be generally non-abrasive so as to limit any discomfort experienced by a patient undergoing treatment.

According to another aspect, the material is disposable. Various methods of providing a disposable positioning paddle are within the scope of the invention. Examples include arranging the material on a two sided frame having mating edge, wherein the mating edges are slid into mating slots of each of the arms 31a and 31b. Alternatively, a disposable or re-usable immobilization paddle may be provided which includes the material as part of the paddle. A switch, dial or other mechanism may be provided on the arms or base of the paddle to increase the 'tightness' of the material. The tightness may be adjusted after the material is positioned over the patient's breast, before the material is placed on the patient's breast, or a combination of both before and after. For example, in one embodiment a mesh screen may be slid into the receptacles within the arm, a dial or other control may provide a first adjustment to the tightness of the screen, the paddle may be moved vertically downward into contact with the breast, and subsequent adjustment to the screen may be used to achieve final immobilization. Alternatively, the mesh material may simply be brought into contact with the breast to a desired compression, as typically done for mammography screening. In still a further embodiment, the arms 31a, 31b, may be coupled to the base 33 of the paddle to permit their movement along the path generally represented by the arrows A in FIG. 3. The immobilization arm of the gantry may be brought down towards the patient's breast with the arms in position A'. When the immobilization arm has reached the desired orientation relative to the patient's breast, the arms may then be brought down into the position shown in FIG. 3, securing the material over the patient's breast and allowing for any tightening that is desired to be performed.

In an alternate embodiment, the arms 31a and 31b are also adjustable along the x-axis, as shown in the arrows B in FIG. 3. Adjustment of the arms in this manner may allow for increased tension to be applied to the breast in the chest area of the patient, while less tension is applied to the nipple, as is sometimes desired for improved tissue capture.

As will be described in more detail below, one benefit of using a material of a porous nature is that it facilitates the application of acoustic couplant during an adjunctive ultrasound procedure. However, it is envisioned that the mesh paddle shown in FIG. 3 may have advantages simply for breast cancer screening, particularly for tomosynthesis screening, which does not generally require the application of high compressive forces such as is used during mammographic imaging. It is recognized that in instances when it is not desired to follow a tomosynthesis scan with an ultrasound review, it may be desirable to provide a system wherein the mesh material may be simply rolled into one of the arms 31b, to provide sanitary material for the next patient. Thus, one embodiment of the invention envisions that the two arms 31a and 31b comprise roller arms, and mechanisms are provided on the arms or at the base for rolling the mesh material from one arm to the other to provide sanitary material for each patient.

As mentioned above, the positioning paddle helps to enable fusion tomosynthesis images and ultrasound images because it allows the patient to remain in a single position during both imaging procedures. Because the patient remains in a fixed position, a one to one correspondence between the x-ray images and ultrasound image feed is made possible. This overcomes problems of the prior art, wherein a ultrasound diagnosis was generally performed by changing a patients position, and the medical professional could only guess that a particular region identified in ultrasound corresponded to the region identified by x-ray.

Many tracking systems are available in the art, and the present invention is not to be limited to any particular tracking system. In addition, many systems are available for merging data obtained from different imaging modalities. However, an additional advantage of the system described herein is that the optical camera of the tracking system is typically in a fixed orientation related to the object to be imaged; i.e., placing the camera on the gantry as shown in the figures provides a reference plane for the tomosynthesis images that facilitates mapping of the coordinate planes for ultrasound. It should be noted, however, that it is not a requirement of the invention that the optical camera of the tracking system be mounted on the gantry.

Figure 4A:
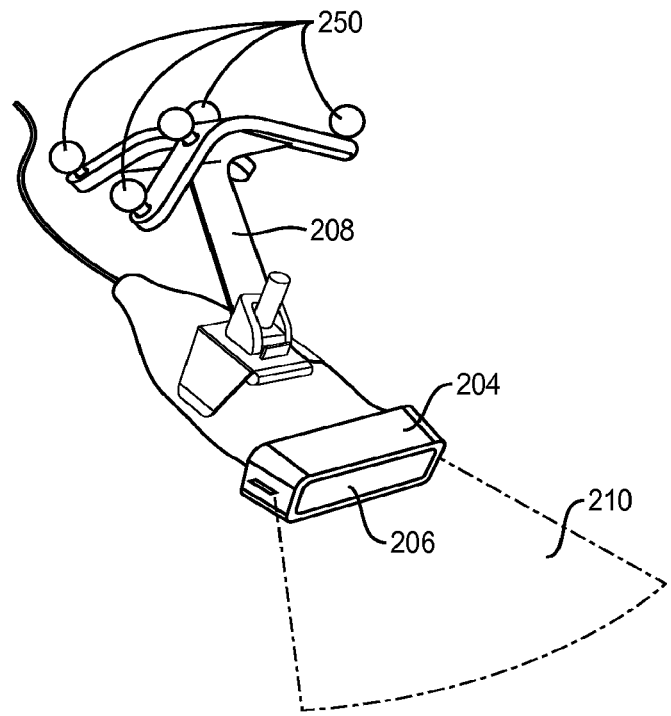
FIGS. 4A and 4B illustrate an exemplary transmitter of a tracking system which may be used in the present invention, the transmitter shown respectively mounted on an ultrasound probe in FIG. 4A, and on a biopsy hand piece in FIG. 4B.
Figure 4B:
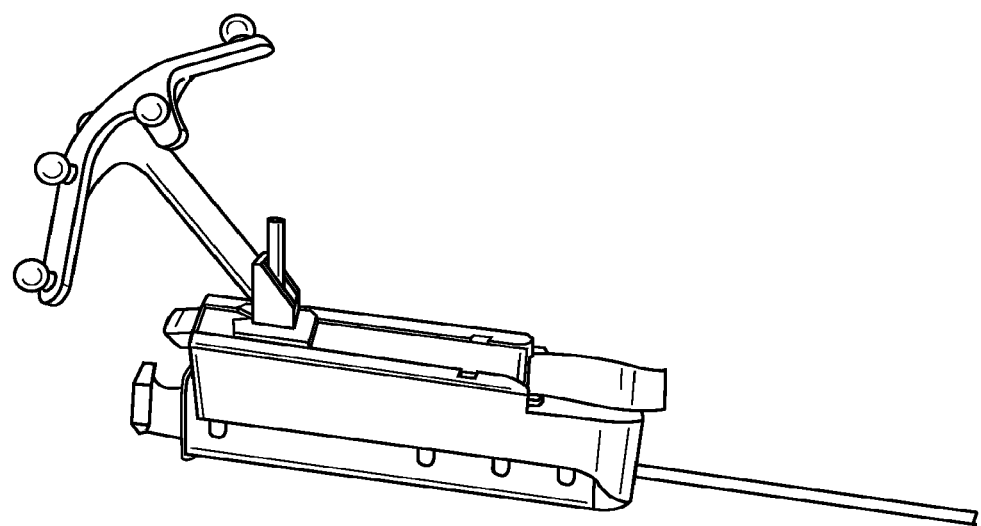

Tracking system 15 comprises optical camera 20 and a plurality of optical transmitters 250, shown in FIG. 4A mounted on an ultrasound probe 204, and in FIG. 4B mounted to a biopsy hand piece; however, skilled persons will understand that alternative tracking systems can be used, such as RF magnetic tracking systems. Optical camera 20 is connected to communication network 12 for transmitting the three dimensional coordinate data of the plurality of optical transmitters to navigation system 13 in the tracker co-ordinate space. Optical camera 20 monitors the position and orientation of ultrasound probe 204 by tracking ultrasound transmitters 250 and transmits this data to navigation system 13 via communication network 12. Skilled persons will appreciate that in some alternative embodiments, optical camera 20 can be connected directly to navigation system 13 via a direct communication link, which may be a physical communication link or a wireless communication link.

In the embodiment shown, ultrasound probe 204 is removably engaged to ultrasound tracker 208 which has ultrasound transmitters 250 that are tracked by optical camera 20 in the tracker co-ordinate space. Skilled persons will appreciate that while in the embodiment shown, ultrasound transmitters 250 are optical transmitters tracked by optical camera 20, other transmitter-receiver systems can be used. For example, in other embodiments, RF transmitters and receivers can be used to track the position and orientation of ultrasound probe 204 in the tracker co-ordinate space. Additionally, skilled persons will appreciate that other orientations and positions of ultrasound transmitters 250 on ultrasound tracker 208 can be used to provide position and orientation information detectable by optical camera 20 and transmitted to navigation system 13. Skilled persons will understand that the use of transmitters that are removably connected to ultrasound probe 204 can tend to provide the ability to configure any ultrasound probe with any shape of transducer, such as linear transducers, curvilinear transducers and array and phased array transducers.

One aspect of the navigation system involves registering the field of view of the ultrasound probe (or, in the case of the biopsy needle, the distal tip of the needle) with the navigation system. The '633 application describes the use of a stylus, which is used to provide certain information to the navigation system related to the width and curvature of the ultrasound probe, and thus the field of view. As described in the '633 application, alternative methods of configuring the probe, including using a pre-generated calibration matrix, may also be used. Similar configuration matrices can be used for interventional devices, such as biopsy needles, where the configuration matrices are customized according to the physical characteristics of the devices. In general, the configuration matrices provide information related to distances between each of the transmitters that are mounted to the device/probe and the relevant points on the device/probe to enable the navigation system to orient and register received images.

In one embodiment, it is envisioned that the 3-dimensional image data and the ultrasound image feed may be used to enable a guided biopsy of the breast, as it is immobilized by the positioning paddle. The biopsy needle may be supported by hand, or via a lateral arm support, and may access the breast from the side or, in configurations where the acoustic gel can be kept away from the biopsy entry point, through the mesh itself.

In an additional embodiment it is realized that the co-registration of the ultrasound image feed with the tomosynthesis slices facilitates capture of ultrasound images at different planes that correspond to the tomosynthesis image planes. Captured ultrasound images, each acquired from parallel planes within the breast, can be reconstructed to generate a three dimensional volume of ultrasound data. The present invention can be used to navigate the ultrasound probe to an appropriate location within a three dimensional volume acquired using tomosynthesis. Once the probe is in the appropriate location, in relating to the three dimensional volume, a sequence of ultrasound images may be obtained at varying depths by varying the strength of the ultrasound signal, thereby generating the information for the corresponding ultrasound image volume. It should be recognized that the present invention is not limited to generation of such a three dimensional ultrasound image volume at any particular location during an examination.

Figure 5:
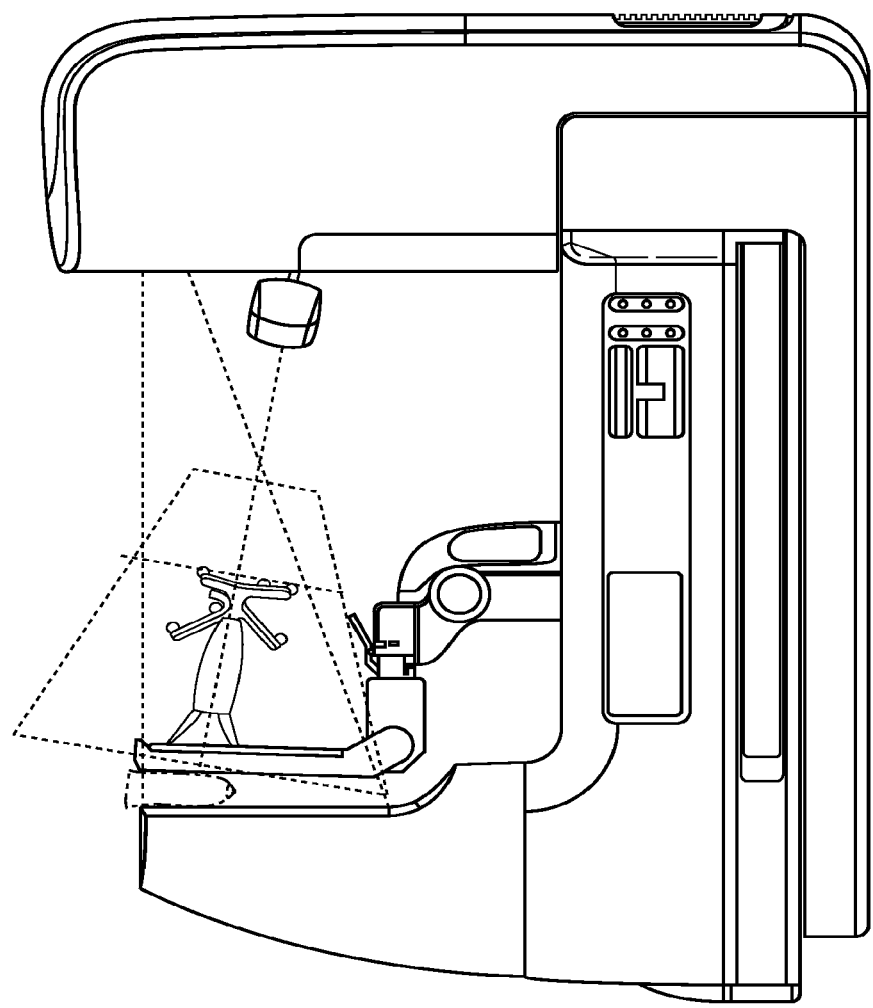
FIG. 5 illustrates the x-ray gantry of FIG. 2, shown with an ultrasound probe having a tracking system transmitter mounted thereon.

For example, FIG. 5 illustrates the different coordinate planes of the ultrasound transducer (in a particular position), and the 3-D tomosynthesis imaging geometry, indicated generally by the cone beam originating from the x-ray tube head. The tracking system uses information provided by the transmitters on the probe to determine the orientation and position of the ultrasound probe in real-time, and therefore provides information related to the particular viewing plane associated with ultrasound feed at any instant.

The real time information provided via the ultrasound image feed can be used in a variety of manners. In one embodiment, after a region of interest in the 3 Dimensional data set is identified, i.e., by selecting a region of interest on a slice, for example, the 3-D image may be held stable and may be displayed at a workstation. Manual manipulation of the ultrasound probe may be performed, with ultrasound image feed being provided on the ultrasound display (or a portion of the workstation display allocated to the ultrasound image). As the ultrasound probe approaches the region of interest, (i.e., as the ultrasound probe is moved into a position which corresponds to the x,y,z coordinates or the ROI in the 3D volume), a visual or audible cue may be provided to the user, allowing the user to view the mass in the different modality, and/or capture a representative image for later review.

In another embodiment, calibration matrices and dynamic reconstruction techniques can be used to dynamically reconstruct the tomosynthesis volume along the imaging plane of the ultrasound transducer. It is appreciated that a tomosynthesis volume set is quite large, and it may not be practical to perform a continuous reconstruction in this manner, but rather provide a user interface that enables the user to reconstruct the selected plane on-the-fly should the medical professional identify a region of interest in the ultrasound image feed. A method for reconstructing tomosynthesis volumes along variable planes is described in more detail in U.S. Patent Ser. No. 61/556,384, filed Nov. 7, 2011 and entitled "SYSTEM AND METHOD FOR SELECTABLE PLANE RECONSTRUCTION OF BREAST TOMOSYNTHESIS IMAGES", incorporated herein by reference.

Figure 6:
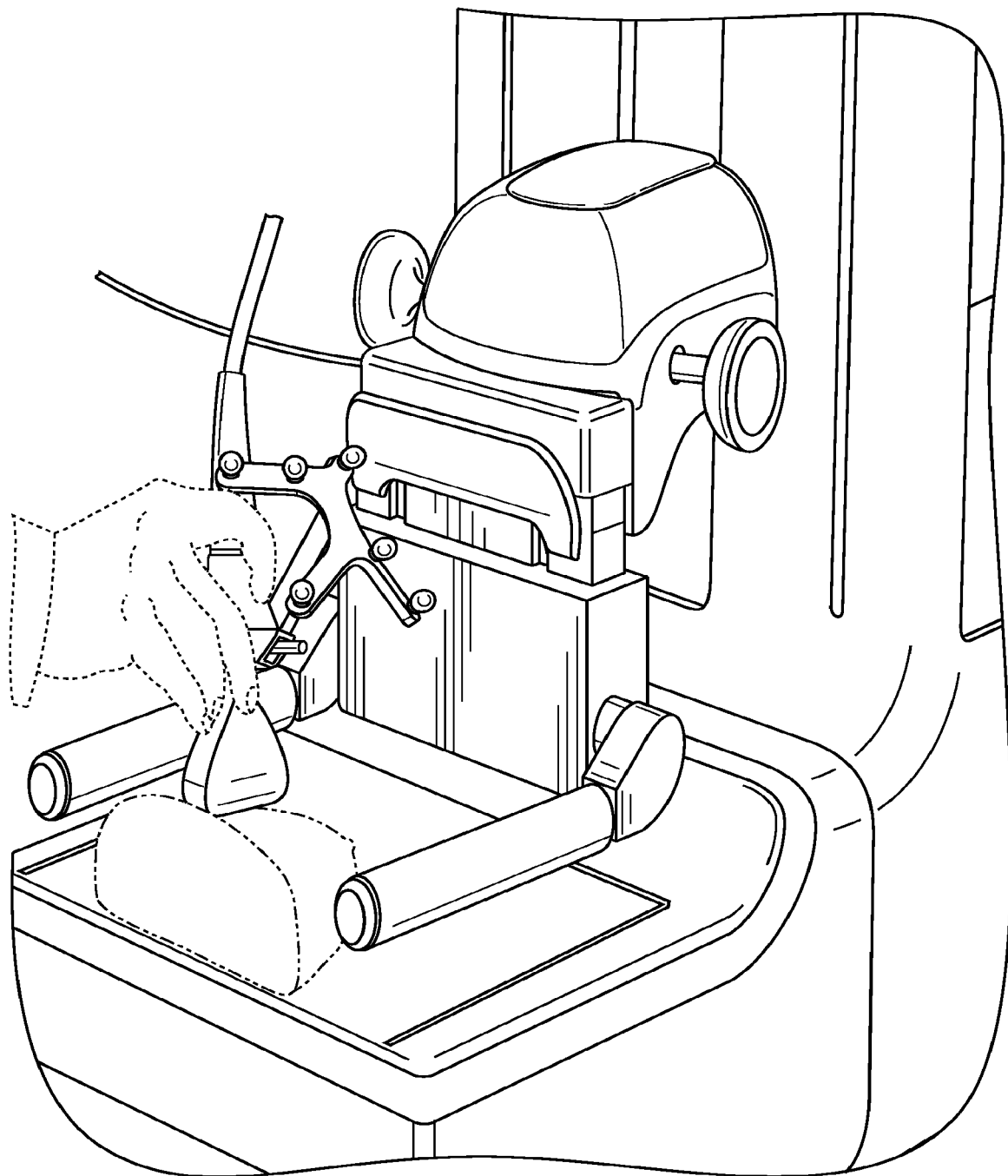
FIG. 6 is an exemplary illustration of an ultrasound acquisition using the transmitting ultrasound probe shown in FIG. 5.

FIG. 6 illustrates an ultrasound probe having transmitters mounted thereon, performing an ultrasound scan on a phantom while the phantom is positioned upon a housing of a detector of a three dimensional tomosynthesis system.

Figure 7:
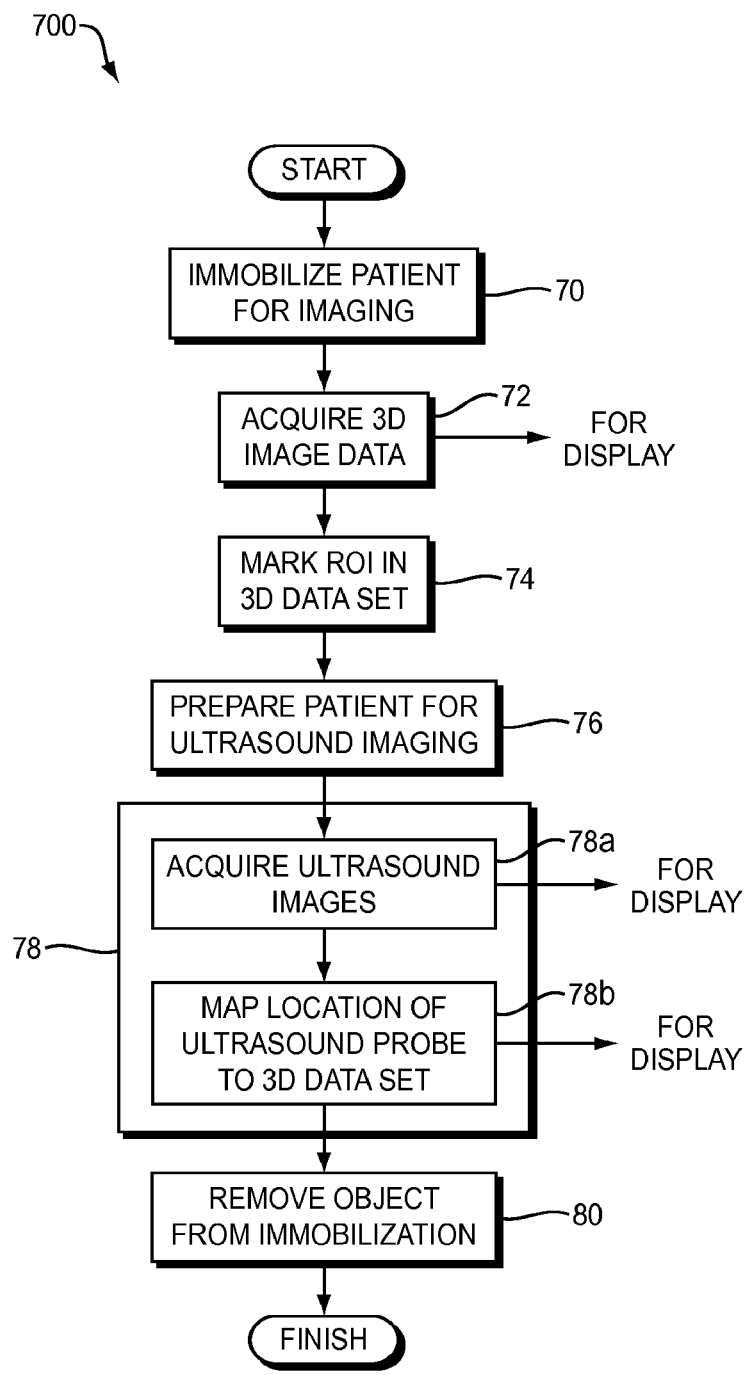
FIG. 7 is a flow diagram illustrating exemplary steps in a diagnosis process which integrates three dimensional x-ray data with real-time ultrasound data.

FIG. 7 is a flow diagram illustrating one exemplary sequence of steps in a process 700 for examining a patient using multiple different imaging modalities for diagnosis purposes while the patient remains in a fixed position. At step 70 the patient is immobilized, for example using the positioning paddle as described above. At step 72 the 3-D image data is captured, for example using tomosynthesis, CT, PET, SPECT, gamma or other imaging technique. This 3-D image data may be displayed on a display device, which is viewable by a user, enabling a user to select an area of interest for further review. At step 74, the region of interest (ROI) is identified or otherwise selected. Selection may be manual, or may automatically be selected using computer assisted detection (CAD) software, or may include a combination of both techniques. At step 76, while remaining immobilized, is prepared for ultrasound imaging. For example, acoustic couplant may be applied to the surface of the positioning paddle. Step 78, the 'diagnosis' step, involves scanning the breast using the ultrasound probe to acquire images and comparing the images against the selected ROI until the ROI is viewed in both modalities. Once diagnosis is completed, at step 80 the positioning paddle may be withdrawn and the patient may be released from their position.

Figure 8:
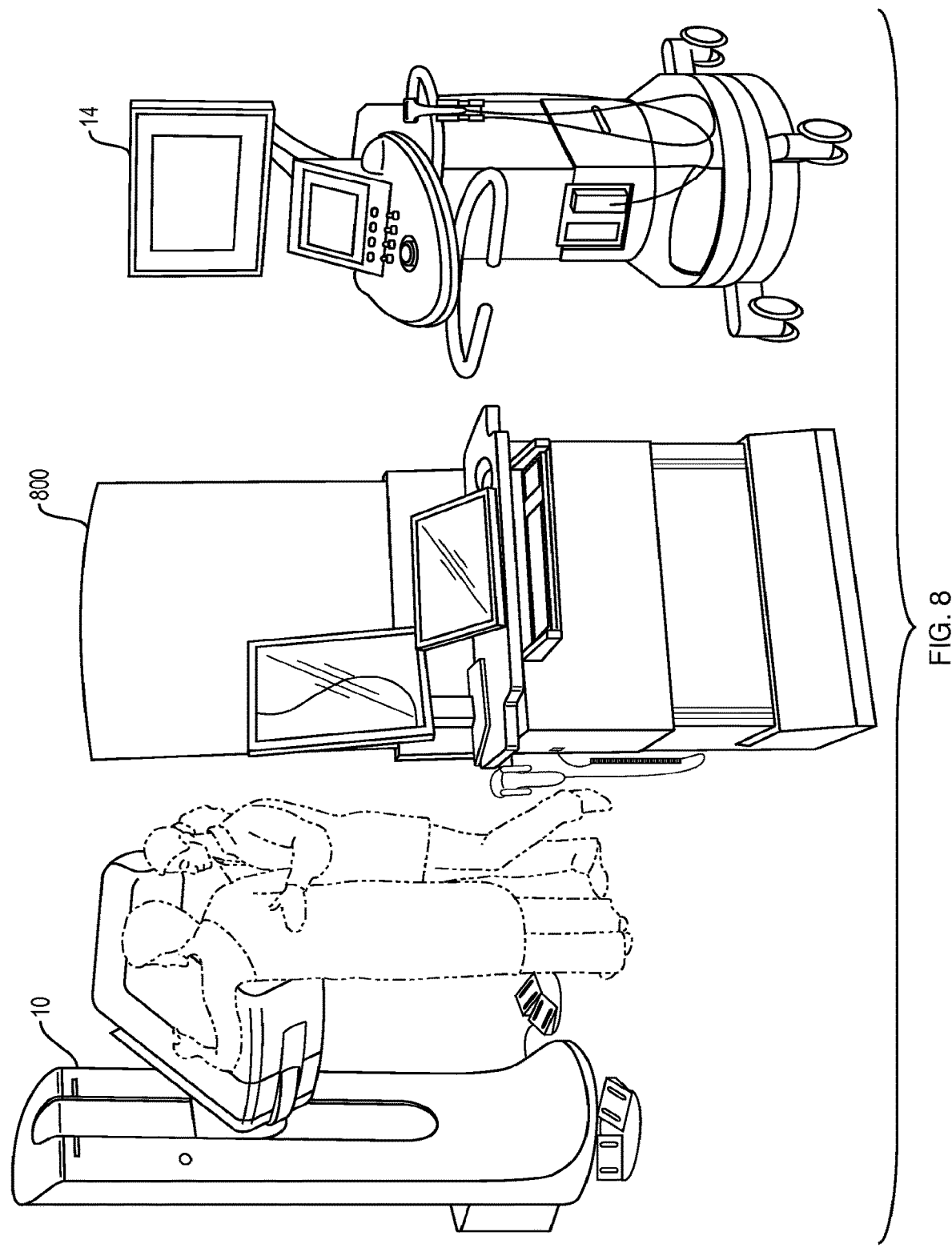
FIG. 8 illustrates equipment which may be included in a radiology suite to enable the performance of the method of FIG. 7.

FIG. 8 illustrates is a pictorial representation of equipment which may be included in a radiology suite capable of performing breast cancer screening and diagnosis while a patient remains in one upright, fixed position. The suite includes a tomosynthesis acquisition system 10, an ultrasound system 14 and a workstation 800. The navigation system and tracking system may be embodied in hardware devices such as those described above with regard to FIGS. 1-7, and software which may be embodied as computer programs loaded onto the workstation 800, which are operable when executed on by a process of the workstation to perform the tasks identified above.

Accordingly, a multi-modality cancer screening and diagnosis system has been shown and described that allows a cancer screening and diagnosis of a patient using at least two different and sequential three-dimensional imaging techniques without the need to reposition the patient. A positioning paddle suitable for use with two different and distinct imaging modalities allows a patient to remain in a fixed position throughout a multi-mode imaging diagnostic process. Tracking and navigation software facilitate image guided diagnosis. As a result, the speed and accuracy of diagnosis may be greatly improved.

Having described several exemplary embodiments, it will be appreciated that numerous specific details have been set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods that have been described herein may be implemented in hardware or software, or a combination of both. In an embodiment these systems and methods are implemented in computer programs executing on programmable computers each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, or cellular telephone. Program code is applied to input data to perform the functions described herein and generate output information. The output information is applied to one or more output devices, in known fashion.

Each program can be implemented in a high level procedural or object oriented programming and/or scripting language to communicate with a computer system. However, the programs can be implemented in assembly or machine language, if desired. In any case, the language may be a compiled or interpreted language. Each such computer program can be stored on a storage media or a device (e.g. ROM or magnetic diskette) readable by a general or special purpose programmable computer, for configuring and operating the computer when the storage media or device is read by the computer to perform the procedures described herein. The embodiments may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Therefore, having described numerous embodiments, it is understood that the present invention is not limited merely to those embodiment, but includes rather includes equivalents thereto. The invention should therefore be only be limited by the attached claims.

What we claim is:

1. A system for imaging a patient breast, the system comprising:
   an imaging gantry comprising a compression arm;
   a positioning paddle adapted to position the breast for imaging by a plurality of imaging modalities of the system, wherein each imaging modality of the plurality of imaging modalities comprises a separate co-ordinate space, wherein the positioning paddle includes:
      a mechanism for coupling the positioning paddle to the compression arm;
      a base;
      an adjustable frame comprising a first portion and a second portion, wherein the first portion and the second portion each have a first end that is attached to the base and a free second end; and
      a material spanning the frame, wherein tension is at least partially applied to the material by moving the free second end of the first portion relative to the free second end of the second portion along a plane defined by the span of the material while the first end of both the first portion and the second portion remains positioned on the base, and wherein the tension applied to the material proximate the free second end of both the first portion and the second portion is greater than the tension applied to the material proximate the first end of both the first portion and the second portion;
   a first imaging system comprising a tomosynthesis system and coupled to the imaging gantry;
   a communication system coupled to the imaging gantry;
   a second imaging system comprising an ultrasound system and coupled to the communication system;
   a tracking system coupled to the second imaging system, wherein the tracking system is configured to track movement of a probe of the second imaging system; and
   a navigation system coupled to the tracking system and the first imaging system, wherein the navigation system is configured to transform a position and an orientation of a field of view of the probe of the second imaging system so that the navigation system co-registers data from the first imaging system and the second imaging system.

2. The system of claim 1, wherein the first imaging system further comprises a system selected from a group including: mammography, computed tomography, SPECT, PET and gamma imaging.

3. The system of claim 1, wherein the material spanning the frame is radiolucent.

4. The system of claim 3, wherein the radiolucent material comprises at least one of an inelastic material and a limited-elasticity material.

5. The system of claim 3, wherein the radiolucent material comprise a mesh material.

6. The system of claim 3, wherein the radiolucent material is positionable relative to the frame.

7. The system of claim 3, wherein the radiolucent material is porous.

8. The system of claim 1, wherein the positioning paddle is positionable relative to the compression arm.

9. The system of claim 1, further comprising a platform for supporting the breast during a multi-modal imaging procedure, wherein at least a portion of the positioning paddle is deflectable relative to the platform when positioning the breast during the multi-modal imaging procedure.

10. The system of claim 9, wherein the positioning paddle is pivotable relative to the compression arm.

11. A multi-modal imaging system for imaging a patient breast, the system comprising:
   an imaging gantry comprising a support platform for supporting the breast and a compression arm movable relative to the support platform;
   a communication system coupled to the imaging gantry;
   a first imaging system coupled to the communication system for performing a first imaging operation of the breast, wherein a first portion of the first imaging system is movably disposed on a first side of the support platform and wherein a second portion of the first imaging system is movably disposed on a second side of the support platform;

a second imaging system different than the first imaging system and coupled to the communicating system for performing a second imaging operation of the breast;

a positioning paddle adapted to maintain a position of the breast for imaging by the multi-modal imaging system during imaging procedures by both the first imaging system and the second imaging system, wherein the positioning paddle comprises:

a base removably coupled to the compression arm;

a pair of opposing arms attached to the base and adjustable in at least two different directions, wherein each arm of the pair of opposing arms comprise a first end coupled to the base and a free second end, wherein the free second end of at least one arm of the pair of opposing arms is moveable relative to the free second end of the other arm of the pair of opposing arms in a first direction that is away from each other, and the pair of opposing arms are pivotable about the first ends relative to the base in a second direction, and wherein the first direction is substantially orthogonal to the second direction; and a material spanning the pair of opposing arms, wherein the first direction of movement of the pair of opposing arms is along a plane defined by the span of the material; and a navigation system coupled to the first imaging system and the second imaging system, wherein the navigation system is configured to transform a position and an orientation of a field of view of the second imaging system so that the navigation system co-registers data from the first imaging system and the second imaging system.

12. The system of claim 11, wherein the second imaging system comprises a component configured to contact the positioning paddle during the second imaging operation.

13. The system of claim 11, wherein the positioning paddle comprises a rigid portion and a flexible portion.

14. The system of claim 13, wherein the flexible portion is configured to deflect relative to the support platform.

15. The system of claim 11, wherein at least a portion of the material comprises a flexible, radiolucent, porous material.

16. The system of claim 11, further comprising an adjustment element to adjust a tension of at least a portion of the positioning paddle.

* * * * *